United States Patent
Hohm et al.

(10) Patent No.: US 10,792,194 B2
(45) Date of Patent: Oct. 6, 2020

(54) APPARATUS AND METHODS FOR SECURING ELASTIC TO A CARRIER WEB

(71) Applicant: Curt G. Joa, Inc., Sheboygan Falls, WI (US)

(72) Inventors: Gottfried Jason Hohm, Sheboygan Falls, WI (US); Wei Wei, North Hollywood, CA (US); Debra Heus Bowe, Kiel, WI (US); Jeff Middlesworth, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 18 days.

(21) Appl. No.: 14/836,698

(22) Filed: Aug. 26, 2015

(65) Prior Publication Data

US 2016/0058624 A1    Mar. 3, 2016

Related U.S. Application Data

(60) Provisional application No. 62/041,876, filed on Aug. 26, 2014.

(51) Int. Cl.
    *A61F 13/15*    (2006.01)
    *A61F 13/49*    (2006.01)
    (Continued)

(52) U.S. Cl.
    CPC .... *A61F 13/15593* (2013.01); *A61F 13/4902* (2013.01); *A61F 13/49009* (2013.01);
    (Continued)

(58) Field of Classification Search
    CPC ................................................ A61F 13/15593
    See application file for complete search history.

(56) References Cited

U.S. PATENT DOCUMENTS

| 3,580,783 A | 5/1971 | Glaz |
| 3,622,434 A | 11/1971 | Newman |

(Continued)

FOREIGN PATENT DOCUMENTS

| CN | 101868210 B | 9/2014 |
| EP | 0274752 | 5/1990 |

(Continued)

OTHER PUBLICATIONS

Presentation by Thomas Ehlert, VP of RD&E, Aurizon Ultrasonics, LLC, entitled "Adhesive-free, Ultrasonic Elastic Attachment", date unknown, 57 pages.

(Continued)

*Primary Examiner* — Ian A Rummel
(74) *Attorney, Agent, or Firm* — Ziolkowski Patent Solutions Group, SC (57) ABSTRACT

Apparatus and methods are provided to allow for creation an elastic laminate. Non-stretched elastic can be laid at peaks over a nonwoven layer contained in valleys and atop peaks. Stretched elastic can be laid over tented nonwoven to create nonwoven tunnels when a second nonwoven is laid atop the first nonwoven and elastic, and the tunnels resist un-stretching of stretched elastic strands by frictional or obstruction forces. A laminated material comprising a first and second layer of material bonded at spaced apart bond sites is disclosed, with a plurality of elastic strands disposed in a non-linear manner between said first and second layer of material, so that said strands meander in a cross-machine direction and traverse a machine direction line, restraining movement of the strands by frictional forces between the strands and the non-woven layers.

19 Claims, 6 Drawing Sheets

(51) Int. Cl.
   *B29C 65/00*        (2006.01)
   *B29C 65/08*        (2006.01)
   *B29L 31/48*        (2006.01)

(52) U.S. Cl.
   CPC ........ *B29C 65/086* (2013.01); *B29C 66/1122*
         (2013.01); *B29C 66/21* (2013.01); *B29C*
         *66/433* (2013.01); *B29C 66/7294* (2013.01);
         *B29C 66/81429* (2013.01); *B29C 66/81431*
         (2013.01); *B29C 66/81433* (2013.01); *B29C*
         *66/81465* (2013.01); *B29C 66/83411*
         (2013.01); *B29C 66/83415* (2013.01); *B29C*
         *66/83511* (2013.01); *B29C 66/221* (2013.01);
         *B29C 66/234* (2013.01); *B29K 2995/0046*
         (2013.01); *B29L 2031/4878* (2013.01)

(56) References Cited

U.S. PATENT DOCUMENTS

| | | |
|---|---|---|
| 3,658,064 A | 4/1972 | Pociluyko |
| 3,668,054 A | 6/1972 | Stumpf |
| 3,982,988 A | 9/1976 | Heimberger |
| 4,088,731 A | 5/1978 | Groome |
| 4,305,988 A | 12/1981 | Kocher |
| 4,333,978 A | 6/1982 | Kocher |
| 4,336,203 A | 6/1982 | Zucker et al. |
| 4,485,819 A | 12/1984 | Igl |
| 4,770,656 A | 9/1988 | Proxmire et al. |
| 4,808,176 A | 2/1989 | Kielpikowski |
| 4,833,734 A | 5/1989 | Estephanian |
| 4,834,738 A | 5/1989 | Kielpikowski et al. |
| 4,842,596 A | 6/1989 | Kielpikowski et al. |
| 5,094,717 A | 3/1992 | Manning et al. |
| 5,163,932 A * | 11/1992 | Nomura ............ A61F 13/49009 2/401 |
| 5,353,798 A | 10/1994 | Sieben |
| 5,468,320 A | 11/1995 | Zafiroglu |
| 5,530,979 A | 7/1996 | Whitley |
| 5,624,420 A | 4/1997 | Bridges et al. |
| 5,769,993 A | 6/1998 | Baldauf |
| 5,789,065 A | 8/1998 | Haffner et al. |
| 5,797,895 A | 8/1998 | Widlund et al. |
| 5,934,275 A | 8/1999 | Gazzara |
| 6,057,024 A | 5/2000 | Mleziva et al. |
| 6,197,404 B1 | 3/2001 | Varona |
| 6,217,889 B1 | 4/2001 | Lorenzi et al. |
| 6,235,137 B1 | 5/2001 | Eperen et al. |
| 6,291,039 B1 * | 9/2001 | Combe ............... A41D 27/245 156/164 |
| 6,295,714 B1 | 10/2001 | Roychowdhury et al. |
| 6,482,278 B1 | 11/2002 | McCabe et al. |
| 6,506,474 B2 | 1/2003 | Tsuji |
| 6,541,679 B2 | 4/2003 | Betrabet et al. |
| 6,613,955 B1 | 9/2003 | Lindsay et al. |
| 6,623,837 B2 | 9/2003 | Morman et al. |
| 6,673,980 B1 | 1/2004 | Varona et al. |
| 6,712,922 B2 | 3/2004 | Sorenson et al. |
| 6,730,188 B2 | 5/2004 | Sanders |
| 6,761,710 B2 | 7/2004 | D'Acchioli et al. |
| 6,780,263 B2 | 8/2004 | Delisle |
| 6,843,872 B2 | 1/2005 | Morman |
| 6,889,622 B2 | 5/2005 | Marcangelo |
| 6,914,018 B1 | 7/2005 | Uitenbroek et al. |
| 6,953,452 B2 | 10/2005 | Popp et al. |
| 7,008,496 B2 | 3/2006 | Morman |
| 7,021,227 B2 | 4/2006 | Marcangelo |
| 7,025,841 B2 | 4/2006 | Owen |
| 7,118,558 B2 | 10/2006 | Wu et al. |
| 7,198,688 B2 | 4/2007 | Mortell et al. |
| 7,211,531 B2 | 5/2007 | Schneider et al. |
| 7,361,241 B2 | 4/2008 | Barth et al. |
| 7,378,566 B2 | 5/2008 | Soerens et al. |
| 7,469,427 B2 | 12/2008 | Yang et al. |
| 7,507,680 B2 | 3/2009 | Middlesworth et al. |
| 7,582,348 B2 | 9/2009 | Ando et al. |
| 7,617,787 B2 | 11/2009 | Marcangelo |
| 7,619,167 B2 | 11/2009 | Lee et al. |
| 7,642,398 B2 | 1/2010 | Järpenberg et al. |
| 7,691,138 B2 | 4/2010 | Stenzel et al. |
| 7,708,849 B2 | 5/2010 | McCabe |
| 7,799,967 B2 | 9/2010 | Ranganathan et al. |
| 7,833,369 B2 | 11/2010 | Zhou et al. |
| 7,901,392 B2 | 3/2011 | Kline et al. |
| 7,981,231 B2 | 7/2011 | Schneider et al. |
| 8,007,484 B2 | 8/2011 | McCabe et al. |
| 8,109,916 B2 | 2/2012 | Wennerbäck |
| 8,142,411 B2 | 3/2012 | Kline et al. |
| 8,182,624 B2 | 5/2012 | Handziak |
| 8,207,395 B2 | 6/2012 | Soerens et al. |
| 8,268,444 B2 | 9/2012 | Okaya |
| 8,298,205 B2 | 10/2012 | Norrby et al. |
| 8,323,257 B2 | 12/2012 | Melik et al. |
| 8,328,820 B2 | 12/2012 | Diamant et al. |
| 8,435,223 B2 | 5/2013 | Roe et al. |
| 8,470,946 B1 | 6/2013 | Carlson |
| 8,585,667 B2 | 11/2013 | Roe et al. |
| 8,647,319 B2 | 2/2014 | Een et al. |
| 8,652,114 B2 | 2/2014 | Roe et al. |
| 8,652,115 B2 | 2/2014 | Roe et al. |
| 8,669,409 B2 | 3/2014 | Roe |
| 8,741,083 B2 | 6/2014 | Wennerbäck et al. |
| 8,758,786 B2 | 6/2014 | Hassler |
| 8,784,395 B2 | 7/2014 | Roe et al. |
| 8,784,397 B2 | 7/2014 | Chang et al. |
| 8,808,263 B2 | 8/2014 | Roe et al. |
| 8,926,579 B2 | 1/2015 | Wang et al. |
| 8,932,273 B2 | 1/2015 | Roe et al. |
| 8,936,586 B2 | 1/2015 | Roe |
| 8,992,497 B2 | 3/2015 | Roe et al. |
| 8,998,870 B2 | 4/2015 | Roe |
| 9,011,402 B2 | 4/2015 | Roe et al. |
| 9,060,905 B2 | 6/2015 | Wang et al. |
| 9,078,789 B2 | 7/2015 | Wang et al. |
| 9,078,792 B2 | 7/2015 | Ruiz |
| 9,089,456 B2 | 7/2015 | Roe et al. |
| 9,095,478 B2 | 8/2015 | Roe |
| 9,180,059 B2 | 11/2015 | Roe et al. |
| 9,301,881 B2 | 4/2016 | Ando et al. |
| 9,387,138 B2 | 7/2016 | Roe |
| 9,539,735 B2 | 1/2017 | Ferguson et al. |
| 2001/0025683 A1 | 10/2001 | Burriss et al. |
| 2001/0034508 A1 | 10/2001 | Betrabet et al. |
| 2001/0044250 A1 | 11/2001 | Tsuji |
| 2002/0092604 A1 | 7/2002 | McCabe et al. |
| 2002/0116027 A1 | 8/2002 | Egan et al. |
| 2002/0119288 A1 | 8/2002 | Morman et al. |
| 2002/0157727 A1 | 10/2002 | Sorenson et al. |
| 2003/0051803 A1 | 3/2003 | Sanders |
| 2003/0120250 A1 | 6/2003 | Betrabet et al. |
| 2003/0124306 A1 | 7/2003 | Morman |
| 2003/0125706 A1 | 7/2003 | Popp et al. |
| 2003/0125707 A1 | 7/2003 | Popp et al. |
| 2003/0135185 A1 | 7/2003 | Crowther |
| 2003/0144643 A1 * | 7/2003 | Jarpenberg ........ A61F 13/15593 604/385.24 |
| 2004/0005832 A1 | 1/2004 | Neculescu et al. |
| 2004/0059280 A1 | 3/2004 | Makower et al. |
| 2004/0112509 A1 | 6/2004 | Morman |
| 2004/0116885 A1 | 6/2004 | Soerens et al. |
| 2004/0127614 A1 | 7/2004 | Jiang et al. |
| 2004/0138635 A1 | 7/2004 | Sorenson et al. |
| 2004/0158217 A1 | 8/2004 | Wu et al. |
| 2004/0192140 A1 | 9/2004 | Schneider et al. |
| 2004/0226645 A1 | 11/2004 | Owen |
| 2004/0243085 A1 | 12/2004 | Veith et al. |
| 2004/0261230 A1 | 12/2004 | Neeb et al. |
| 2005/0095942 A1 | 5/2005 | Mueller et al. |
| 2005/0101216 A1 | 5/2005 | Middlesworth et al. |
| 2005/0142331 A1 | 6/2005 | Anderson et al. |
| 2005/0148261 A1 | 7/2005 | Close et al. |
| 2005/0176029 A1 | 8/2005 | Heller et al. |
| 2005/0183646 A1 | 8/2005 | Marcangelo |
| 2005/0216058 A1 | 9/2005 | Egan et al. |

(56) References Cited

U.S. PATENT DOCUMENTS

| | | |
|---|---|---|
| 2005/0228350 A1 | 10/2005 | Ranganathan et al. |
| 2006/0009104 A1 | 1/2006 | Schneider et al. |
| 2006/0069373 A1 | 3/2006 | Schlinz et al. |
| 2006/0099871 A1 | 5/2006 | Poruthoor et al. |
| 2006/0130964 A1 | 6/2006 | McCabe |
| 2006/0135923 A1 | 6/2006 | Boggs et al. |
| 2006/0135932 A1 | 6/2006 | Abuto et al. |
| 2006/0138693 A1 | 6/2006 | Tuman et al. |
| 2006/0149208 A1 | 7/2006 | Carr |
| 2006/0180068 A1 | 8/2006 | Marcangelo |
| 2006/0224137 A1 | 10/2006 | McCabe et al. |
| 2006/0228969 A1 | 10/2006 | Erdman |
| 2006/0238757 A1 | 10/2006 | Silcott |
| 2006/0270302 A1 | 11/2006 | Ando et al. |
| 2007/0000021 A1 | 1/2007 | Yang et al. |
| 2007/0068529 A1 | 3/2007 | Katatoor et al. |
| 2007/0131335 A1 | 6/2007 | Zhou et al. |
| 2007/0218245 A1 | 9/2007 | Schneider et al. |
| 2007/0286987 A1 | 12/2007 | Anderson et al. |
| 2008/0103460 A1 | 5/2008 | Close et al. |
| 2008/0110554 A1* | 5/2008 | Otsubo ............. A61F 13/15747 156/163 |
| 2008/0262455 A1 | 10/2008 | Soerens et al. |
| 2009/0134049 A1 | 5/2009 | Melik et al. |
| 2009/0163940 A1 | 6/2009 | Sliwa |
| 2009/0208703 A1 | 8/2009 | Wennerback et al. |
| 2009/0242098 A1 | 10/2009 | Handziak |
| 2009/0306616 A1 | 12/2009 | Wennerbäck |
| 2009/0326503 A1 | 12/2009 | Lakso et al. |
| 2010/0015190 A1 | 1/2010 | Hassler |
| 2010/0076390 A1 | 3/2010 | Norrby et al. |
| 2010/0087352 A1 | 4/2010 | Mason |
| 2010/0286709 A1 | 11/2010 | Diamant et al. |
| 2010/0298798 A1 | 11/2010 | Lakso et al. |
| 2010/0324513 A1 | 12/2010 | Wennerbäck |
| 2011/0061786 A1 | 3/2011 | Mason |
| 2011/0118689 A1 | 5/2011 | Een et al. |
| 2011/0152811 A1 | 6/2011 | Bing-Wo et al. |
| 2011/0067797 A1 | 7/2011 | Schneider et al. |
| 2011/0184372 A1 | 7/2011 | Esping Ostlin et al. |
| 2011/0251576 A1 | 10/2011 | Ando et al. |
| 2011/0257616 A1 | 10/2011 | Lakso |
| 2012/0088103 A1 | 4/2012 | Sugiura et al. |
| 2012/0123367 A1 | 5/2012 | Melik et al. |
| 2012/0123368 A1 | 5/2012 | Melik et al. |
| 2012/0123369 A1 | 5/2012 | Melik et al. |
| 2012/0123370 A1 | 5/2012 | Melik et al. |
| 2012/0123371 A1 | 5/2012 | Melik et al. |
| 2012/0123372 A1 | 5/2012 | Melik et al. |
| 2012/0123373 A1 | 5/2012 | Melik et al. |
| 2012/0228988 A1 | 9/2012 | Cutsforth |
| 2012/0321856 A1 | 12/2012 | Afshari |
| 2012/0328841 A1 | 12/2012 | Afshari |
| 2012/0328842 A1 | 12/2012 | Afshari |
| 2013/0011601 A1 | 1/2013 | Fenske |
| 2013/0042411 A1 | 2/2013 | Vitale |
| 2013/0048191 A1 | 2/2013 | Durrance et al. |
| 2013/0079797 A1 | 3/2013 | Diamant et al. |
| 2013/0157012 A1 | 6/2013 | Qin et al. |
| 2013/0165896 A1 | 6/2013 | Carbonari |
| 2014/0093687 A1 | 4/2014 | Humiston et al. |
| 2014/0099469 A1 | 4/2014 | Abuto et al. |
| 2014/0102650 A1 | 4/2014 | Qin et al. |
| 2014/0180126 A1 | 6/2014 | Millett et al. |
| 2016/0288407 A1 | 10/2016 | Ehlert et al. |
| 2016/0331600 A1 | 11/2016 | Polidori et al. |

FOREIGN PATENT DOCUMENTS

| | | |
|---|---|---|
| EP | 0168225 | 3/1991 |
| EP | 0330716 | 7/1991 |
| EP | 0307871 | 12/1992 |
| EP | 0386324 | 6/1993 |
| EP | 0886480 B1 | 12/2001 |
| EP | 1166721 | 12/2003 |
| EP | 1388410 A1 | 2/2004 |
| EP | 1035808 | 3/2004 |
| EP | 1024721 | 9/2004 |
| EP | 1351815 | 6/2005 |
| EP | 1448824 | 10/2005 |
| EP | 1236827 | 1/2006 |
| EP | 1029521 | 4/2006 |
| EP | 1138471 | 6/2006 |
| EP | 1159942 | 7/2006 |
| EP | 1641417 | 6/2007 |
| EP | 1555000 | 11/2008 |
| EP | 1290289 | 12/2008 |
| EP | 1330355 | 3/2009 |
| EP | 1263989 | 5/2009 |
| EP | 1458553 | 9/2009 |
| EP | 1330222 | 10/2009 |
| EP | 1610950 | 10/2009 |
| EP | 1715994 | 3/2010 |
| EP | 1520569 | 7/2010 |
| EP | 1586252 | 8/2010 |
| EP | 1959907 | 9/2010 |
| EP | 1525345 | 4/2011 |
| EP | 1882177 | 6/2011 |
| EP | 1707168 | 8/2011 |
| EP | 1716831 | 9/2011 |
| EP | 2083100 | 9/2011 |
| EP | 2207926 | 9/2011 |
| EP | 2219534 | 9/2011 |
| EP | 2431013 | 3/2012 |
| EP | 2027841 | 7/2012 |
| EP | 1595017 | 8/2012 |
| EP | 1891256 | 8/2012 |
| EP | 2020972 | 11/2012 |
| EP | 2020974 | 12/2012 |
| EP | 1685816 | 1/2013 |
| EP | 2024178 | 1/2013 |
| EP | 2088980 | 1/2013 |
| EP | 2103427 | 3/2013 |
| EP | 1272347 | 4/2013 |
| EP | 1458565 | 3/2014 |
| EP | 1575470 | 6/2014 |
| EP | 2088981 | 6/2014 |
| EP | 2441866 | 2/2015 |
| EP | 2727521 | 3/2015 |
| EP | 1806117 | 6/2016 |
| EP | 3092997 B1 | 8/2017 |
| EP | 2116367 | 4/2018 |
| RU | 2304047 C2 | 12/2002 |
| RU | 2010125133 A | 12/2011 |
| WO | WO2009/067055 A1 | 5/2009 |
| WO | WO2011/087502 A1 | 7/2011 |

OTHER PUBLICATIONS

Presentation by Thomas Ehlert, VP of RD&E, Aurizon Ultrasonics, LLC, entitled "Adhesive-free, Ultrasonic Elastic Attachment", date at least as early as Nov. 17, 2014, 57 pages.

* cited by examiner

APPARATUS AND METHODS FOR SECURING ELASTIC TO A CARRIER WEB

RELATED APPLICATION

This application claims the benefit of co-pending U.S. Provisional Patent Application Ser. No. 62/041,876, filed 26 Aug. 2014.

BACKGROUND OF THE INVENTION

This invention relates to an apparatus and method for producing a laminate of elastic material by attaching a non-elongated elastic to a carrier web or webs. While the description provided relates to diaper manufacturing, the apparatus and methods are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The spaced effect of such slicing is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leghole-elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now to receive an insert.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

The current practice in applying a stretchable web such as a poly web to a second web is involved continuously feeding the poly web into the process which results in poly running full length of product, or alternatively, full length of a constructed insert core which is then placed onto a nonwoven-type chassis. Not all machine configurations can be adapted from a full length poly chassis to a poly insert configuration due to space and/or cost restrictions. It should be understood that application of the poly web along the entire length of the product, rather than only where it is useful, increases the amount of poly material which must be utilized. This is a waste of the material resource and adds additional cost to the product. It is therefore desirable to create a lower cost product by putting poly into the product only where it is useful, instead of the complete product.

However, typical slip/cut application of poly patch to a continuous web does not work well because of the elasticity of the poly web. The slip/cut process allows the poly to slip on anvil prior to being cut causing the poly to violently snap back at the moment of cut. This can result in a short patch-long patch output from the slip/cut where one or more of the resulting poly catches are extremely distorted on the carrier web.

In certain instances, it is desirable to eliminate or minimize the use of adhesives in the manufacturing process. This results in a material savings. Also, it is desirable to reduce significant strains applied to elongated elastics that are held under significant strain of 50-400%. At this level of elongation, there is a lot of stress on the elastic and the elastic has an increased likelihood of breaking, which can lead to machine downtime.

In prior art systems, such as U.S. Pat. 6,291,039, it is known to capture elastics between layers of nonwoven materials. For instance, as taught therein, elastics can be placed into a hem of nonwoven material, and when the nonwoven material is bonded onto itself at the hem, the elastic can be captured within the folded over layer of material.

In U.S. Pat. No. 7,642,398 an elasticized web has a gatherable substrate and a multi-strand elastic yarn affixed to the gatherable substrate at a plurality of fixation locations. So that the yarn can be affixed to the substrate without the use of an adhesive, the yarn is subjected to forces to create partial delamination of the yarn at the fixation locations and a portion of the gatherable substrate is caused to pass between the thus delaminated strands of the multi-strand elastic yarn. A patterned surface is disclosed in which the distribution density of raised heels varies over the surface area of the patterned surface. The patterned surface comprises one or more regions along the length of the yarn in which no raised heels are present, so that the elasticized web produced using this patterned surface will have regions along the length of the elastic yarn at which no bonds are present. Accordingly, the elastic yarn will be able to move independently of the substrate or substrates in such regions.

SUMMARY OF THE INVENTION

One aspect of the invention is a method including providing a base non-woven layer, and applying thereto an elastic strand, strip or web. Throughout the specification, nonwoven webs are referred to. The references to nonwoven webs should be considered to extend to bondable webs generally, but alternative web materials are considered within the scope the invention. Examples of bondable webs which could be used in the present invention when nonwovens are referred to, are any film webs, including polypropylene or polyethylene. Commonly elastics are applied under elongation/tension to carrier webs. In the present invention, non-elongated elastics, or elastics at low tension, are provided to a carrier web. In one embodiment, the carrier web is accumulated in valleys and the elastic is bonded to the carrier web at peaks. Such bonding could be done with, but not limited to, adhesives, ultrasonics, or pressure. After bonding, the carrier web is returned to its unaccumulated state thereby elongating the elastic(s) in the process. A simple relationship between the amount of material accumulated and the distance between bond sites determines the final elongation, or strain, of the elastic(s).

In another embodiment of the present invention, elastic filaments can be separated from one another through ultrasonic force, electrostatic separation, or tension on the elastic yarn. With an electrostatic charge on the elastic filaments, the filaments separate and the filaments and nonwoven layer bond with minimal severing of the filaments.

In another aspect of the present invention, elastics are captured within layers of nonwoven materials, with the elastics laid down and captured between the nonwoven layers in a meandering pattern between bond points of nonwoven materials of the laminate. In this configuration, differently shaped and configured pins or protrusions on a roll or drum can urge the elastics to meander between bond points. In other words, the elastics can be trained to run straight, curved, meandering, or any combination of those lay down patterns, and then retained in that laydown position due to friction between the elastic material and the nonwoven material, particularly if the elastics are meandering through non-linear bond points.

Several pin and protrusion configurations (oblong, curved, rectangular, circular) can be used in different patterns on a rotating drum, such as variably spaced patterns, offset patterns, curved patterns or the like, to establish a complex pattern of elastics meandering through bond points in the nonwoven layers capturing the elastics, and the friction between the elastic and the material retains the elastic sufficiently in place to minimized adhesive bonding between the elastics and the nonwoven required to create the laminate.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

It is noted that the present techniques and apparatus are described herein with respect to products such as diapers, but as previously mentioned, can be applied to a wide variety of processes in which discrete components are applied sequentially.

Figure 1:
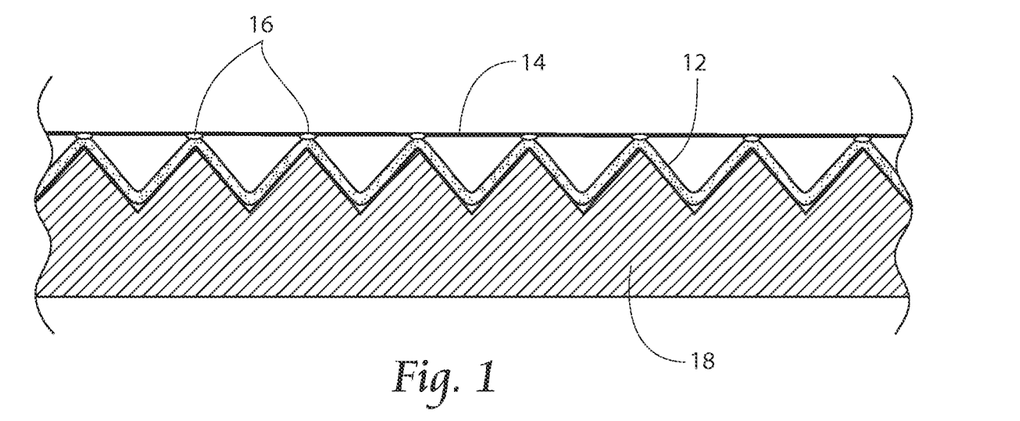
FIG. 1 is a side view of an apparatus and method of forming an elastic laminate.

Referring now to FIG. 1, a side view of an apparatus and method of forming an elastic laminate is shown. A base support structure 18 is provided with peaks and valleys, which can be a "V" shape. A preferably non-woven layer 12 is laid into the valleys. Atop the nonwoven 12 is laid an unstretched or relatively unstretched elastic layer 14, which can comprise strands or a web of elastic. This elastic 14 is bonded to the non-woven layer 12 at bond points 16. Such bonding could be done with, but not limited to, adhesives, ultrasonics, or pressure.

Figure 2:
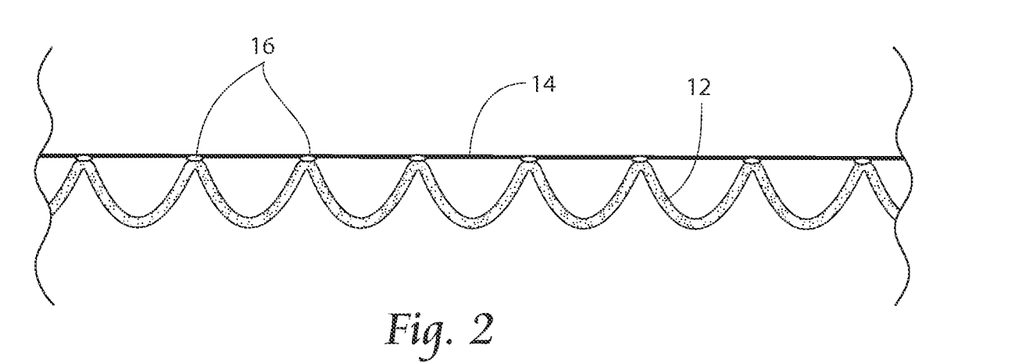
FIG. 2 is a side view of an elastic laminate with an unstretched elastic and a slack base layer.

FIG. 2 is a side view of an elastic laminate with an unstretched elastic 14, and a slack base layer 12, shown just after bonding the two layers together.

Figure 3A:
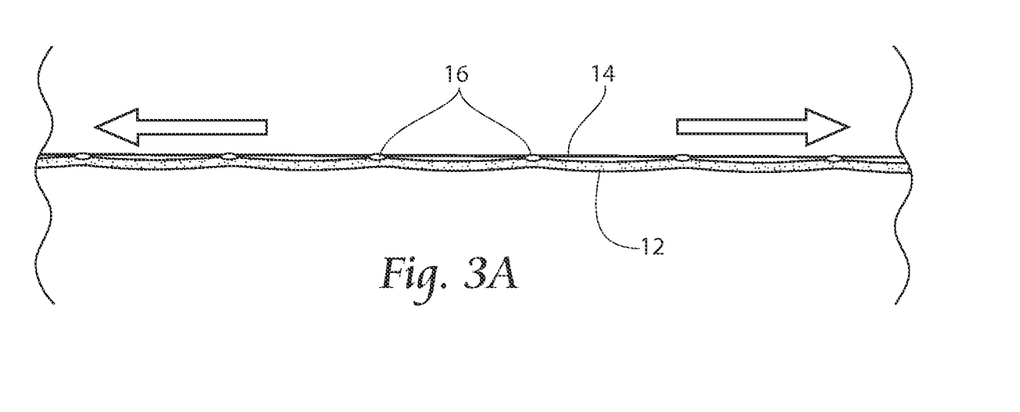
FIG. 3a is a side view of an elastic laminate with a tensioned elastic layer and a stretched or tensioned base layer.

After bonding, the carrier web 12 is returned to its unaccumulated state thereby elongating the elastic(s) 14 in the process, as shown in FIG. 3a. If considered mathematically, a relationship between the amount of material, accumulated within the valleys, and the distance between the peaks determines the final elongation or strain $\in$( ) of the elastics. Twice the distance from peak to valley, divided by the distance between peaks, defines $\in$) ( of the elastics. Put another way, twice the distance from peak to valley will measure the distance between bond points of nonwoven 12 in a non-accumulated state.

Figure 3B:
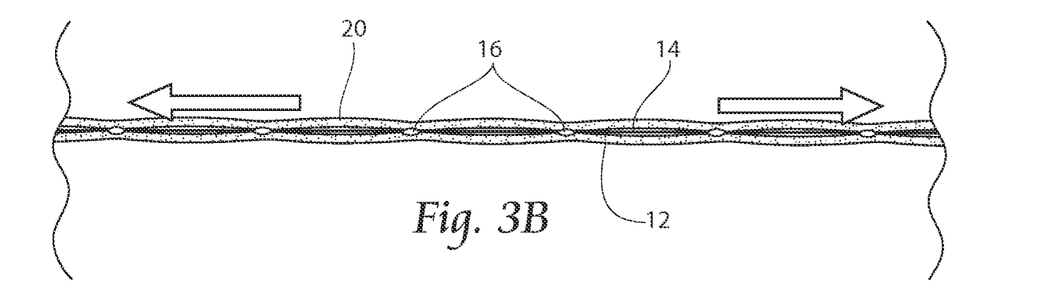
FIG. 3b is a side view of an elastic laminate with a tensioned elastic layer and a stretched or tensioned base layer, and a second material layer coupled to the elastic layer.
Figure 4A:
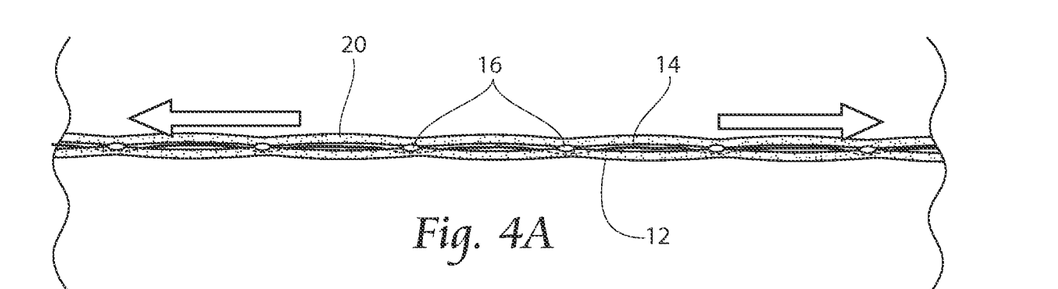
FIG. 4a is a side view of an elastic laminate with a tensioned elastic layer and a stretched or tensioned base layer, and a second material layer coupled to the base layer (or first material layer) at discrete bond points, with the elastic layer positioned between the first and second material layers.

If desired, as shown in FIG. 3b, a second material layer 20 (preferably nonwoven) can be coupled to the elastic 14, or in an alternate configuration, coupled to the first material layer (FIG. 4a).

Figure 4B:
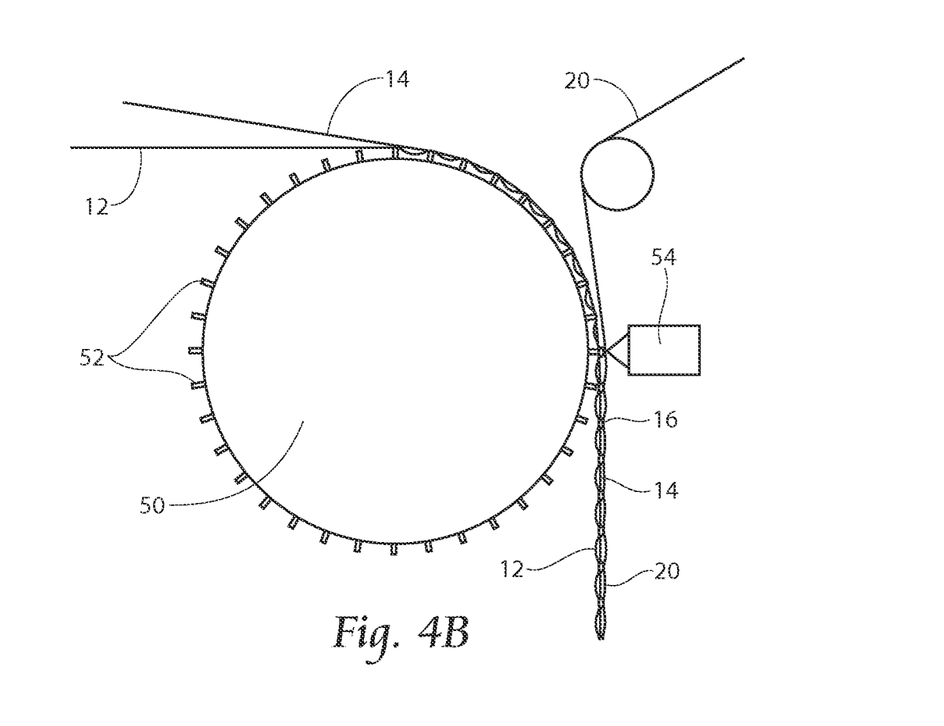
FIG. 4b is a side view of an alternate embodiment of the present invention, with pins (or anvil bond points) placed about an anvil roll and carrying the first material layer, and elastic strands laid atop the first non-woven layer tented by the pins, with a second material layer laid over the elastic strands and first material layer, and trilaminate bonded together and passed downstream for further processing.
Figure 4C:
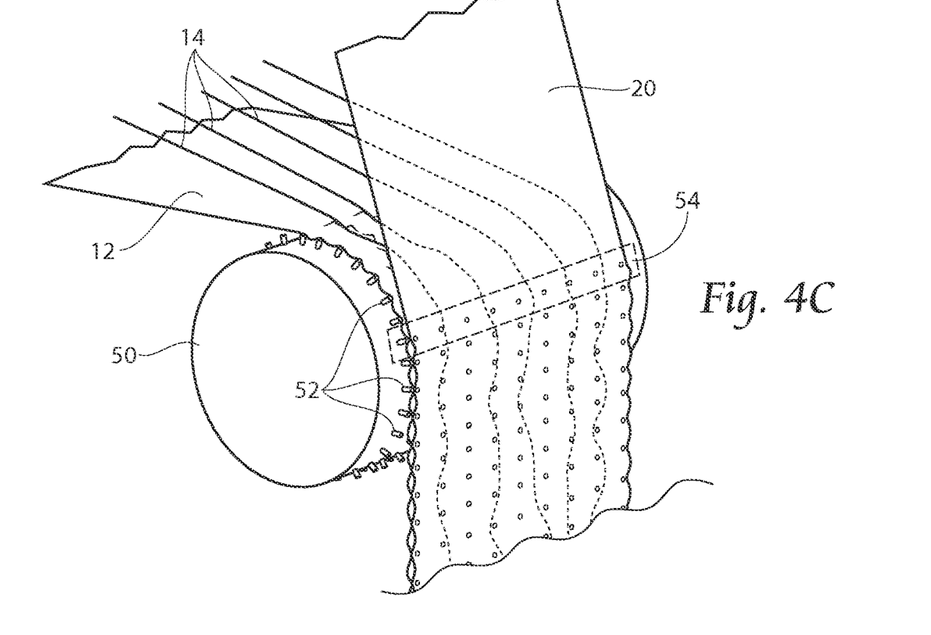
FIG. 4c is a perspective view of the machine of FIG. 4b, with elastic strands laid down atop the first material layer, and the elastic strands allowed to or encouraged to wander about the anvil bond points to be laid down and the first and second layers bonded at the bond points to secure the elastics therebetween in meandering fashion.

In an alternative embodiment of the present invention as shown in FIG. 4b. The forming technique described with reference to FIG. 4a is shown in side view in FIG. 4b. Pins or protrusions or anvil bond points 52 are placed about an anvil roll 50, and elastic strands 14 laid atop a nonwoven layer 12 tented by the pins 52. Adjacent tented nonwoven 12 peaks create somewhat of a tunnel when coupled with top nonwoven 20, and elastic 14 is carried in the tunnel in circuitous or meandering ways as shown in FIG. 4c. The result is that the elastic 14 is restrained from lateral (or cross-machine direction) movement by encountering bond points between the first and second material layers 12 and 20 respectively, created by points 52 acting against ultrasonic horn 54. Alternatively, adhesives can be used in bonding.

Figure 5:
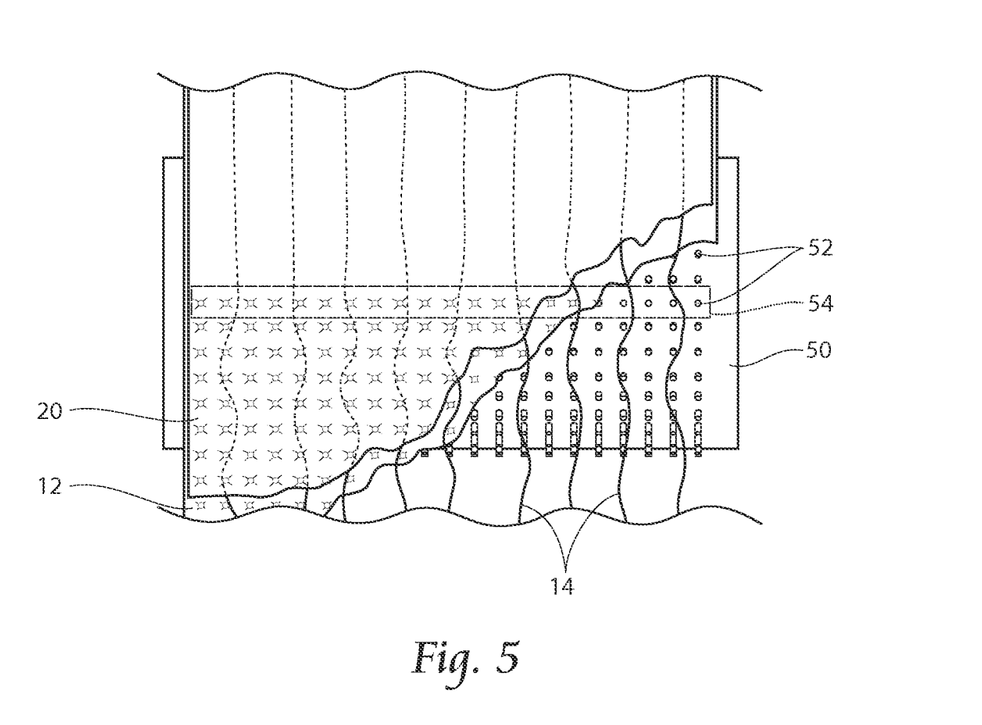
FIG. 5 is a side view of the unit of FIG. 4c, showing the trilaminate formation, with the meandering elastics trapped between the bond points of the first and second layers.

Still referring to FIG. 4c, and also to FIG. 5, protrusions 52 on an anvil roll 50 carry nonwoven 12, and create a tenting effect by raising the portions of the nonwoven 12 carried by the protrusions 52. It is between and about these adjacent and downstream bond points that the elastic 14 is allowed to, or encouraged to, meander generally in the machine direction as opposed to traveling linearly in the machine direction. Elastic 14 is laid down with tension in a circuitous path over and about the protrusions 52. The elastic 14 forces the nonwoven 12 down around protrusions 52 and the protrusions 52 are used to ultrasonically bond a second, top nonwoven layer 20 to the first nonwoven 12. The elastic 14 experiences a fairly high frictional force against the bonded segments of the nonwoven layers 12 because of the serpentine (meandering) path of the elastic 14 about the bond points and against the material layers 12 and 20 themselves, keeping the elastic 14 from creeping.

Figure 4D:
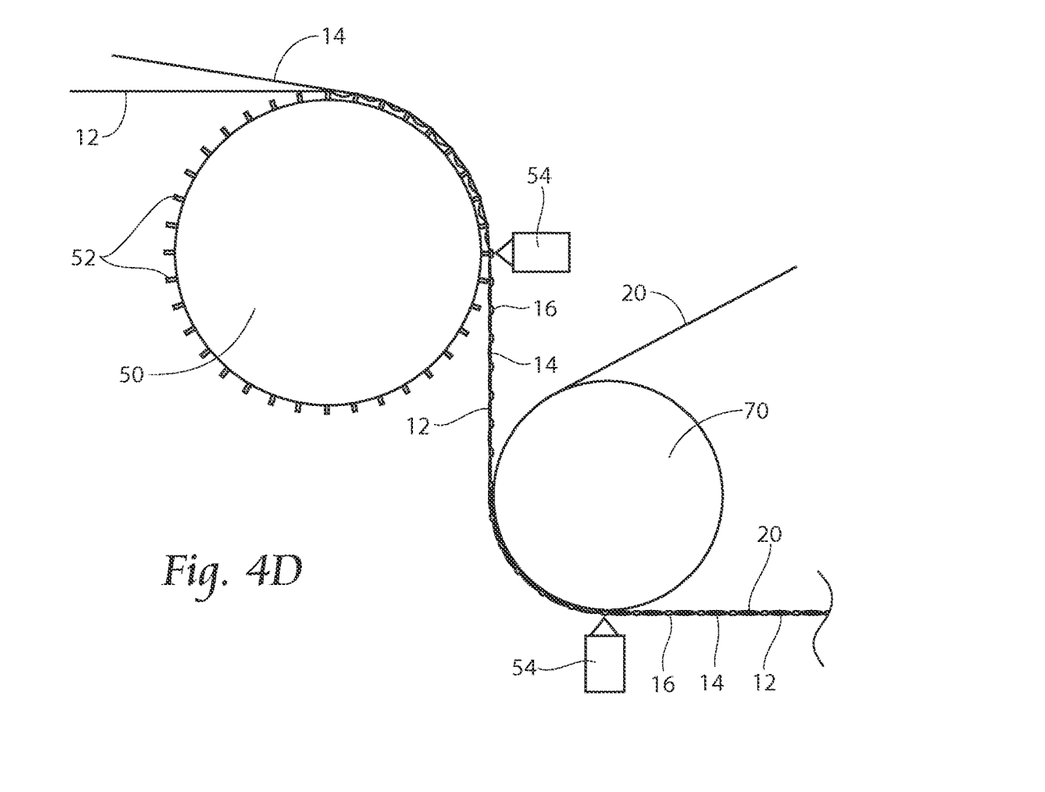
FIG. 4d is a side view of a machine for joining the elastic and first material layer at bond points, bringing first material layer to a taut condition, and bonding a second material layer to the laminate during a second bonding operation.

Referring now to FIG. 4d, a forming technique described with reference to FIG. 3b is shown in side view in FIG. 4. In particular, after joining initially relaxed elastic 14 and initially relaxed first material layer 12 at bond points 16 by bonding unit 54, first material layer 12 and elastic layer 14 can be brought taut by elongating elastic 14. After first material layer 12 is sufficiently taut, second material layer 20 (preferably non woven) is introduced to the laminate 12/14, and a second bonding operation occurs between material layer 20 and laminate 12/14. This bonding can be performed by adhesive (not shown) or by an ultrasonic horn 54 operating against drum 70.

Figure 6:
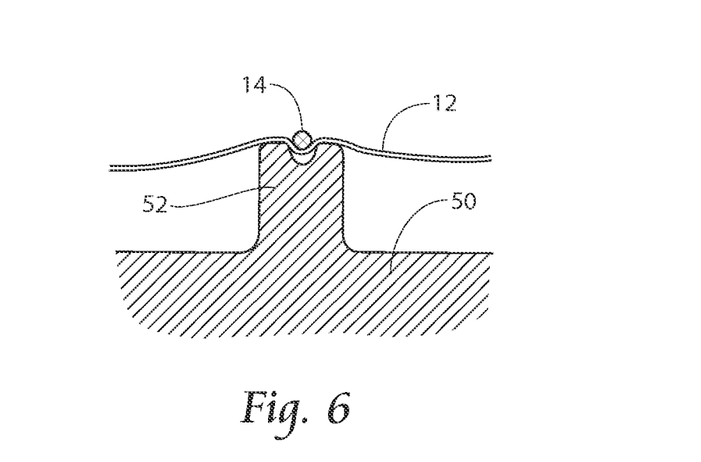
FIG. 6 is an alternate embodiment of the pinned anvil arrangement, with slots provided about the anvil.

Referring now to FIG. 6, an alternate embodiment of the pinned anvil arrangement of FIGS. 4 and 5 is shown, with slots 54 provided about the anvil roll 50. First nonwoven layer 12, and atop that layer, the elastic 14 is laid down in slots 54, and a top nonwoven layer 20 is laid down and bonded to first nonwoven layer 12. This creates a tunnel, of nonwoven, and the tight elastic 14 is resistant to creeping as described previously.

In addition to the techniques described above, modifications to the physical properties of the elastic 14 can assist providing the desired frictional resistance between the elastic 14 and nonwoven 12. For instance, ultrasonic force applied to the strands can cause the strands to unravel; those unraveled ends would choke any created tunnels in the nonwoven. Alternatively or additionally, the nonwoven layers 12 could be bonded through the unraveled strands 14, or could be unraveled without bonding.

Still alternatively or additionally, a polymer coating such as Ethylene Vinyl Acetate (EVA) could be intermittently applied on the stretched elastic strands 14, to create rings or collars of eventually solidified polymer. The eventually solidified polymer on the elastic strands 14 would provide a physical barrier on created or improvised tunnels and might even get bonded into the nonwoven bonds that form the tunnel.

Still alternatively or additionally, two or more elastic strands 14, can be twisted together, those entwined fibers 14 also physically resist travel through the created tunnels as the elastic 14 tries to relax. Additionally, a single elastic strand 14 can be rolled to make a bulky twisted structure that resists creep through the tunnel more effectively than elastic 14 that is simply stretched. Alternatively or additionally, the elastic 14 can be frayed or nicked with a rough surface such as sandpaper; it may pull the individual fibers apart, or roughen the surface to fatten it up.

Figure 7:
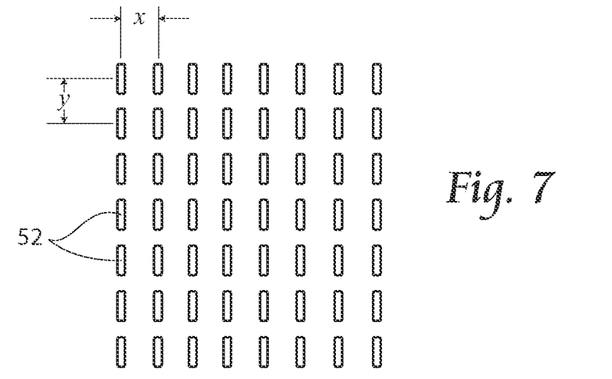
FIG. 7 is an alternate anvil bond point configuration.

Referring now to FIG. 7, an alternate anvil bond point 52 configuration is shown. Bond points 52 are spaced apart in the machine direction by spacing y, and spaced apart in the cross-machine direction by spacing x. X and y can both vary and be variable between adjacent bond points 52. That is, the points can be closely spaced apart in the cross-machine or machine directions, or more distantly spaced apart, and the spacing can vary from one row to the next, and from one column to the next.

Figure 8:
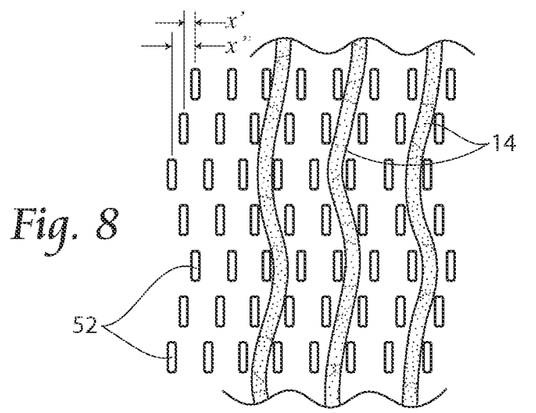
FIG. 8 is a second alternate anvil bond point configuration encouraging circuitous path of the elastic strands about the anvil bond points, the spaces between the anvil bond points (where the first and second material layers will become bonded, creating short tunnels to encourage the lacing action of the elastics between these tunnels to limit creep)

For instance, as shown in a second alternate anvil bond point configuration of FIG. 8, the bond points 52 can be spaced to encourage a circuitous path of the elastic strands 14 about the anvil bond points (noting that in a preferred embodiment that a nonwoven will be draped over the bond points 52 and the nonwoven is not shown in FIG. 8). In this configuration, a cross machine direction spacing x' offset is provided in a column of bond points 52. The spaces between the anvil bond points 52 (where the first and second material layers 12 and 20 will become bonded) creating short tunnels to encourage the lacing action of the elastics 14 between these tunnels to limit creep.

Figure 9:
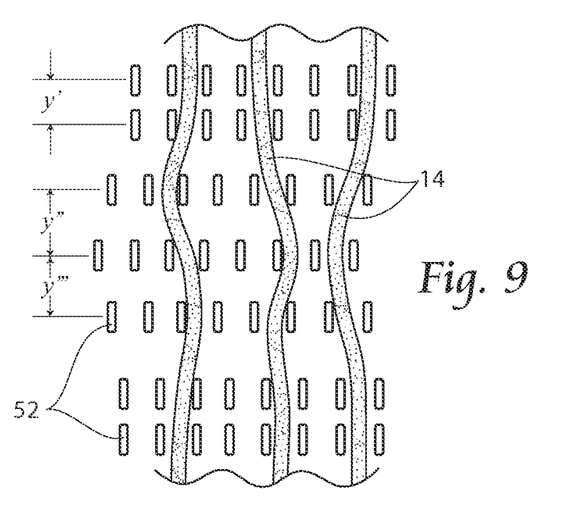
FIG. 9 is a third alternate anvil bond point configuration.

Referring to FIG. 9, third alternate anvil bond point 52 configuration varies machine direction spacing y', y" and y'" by an offset provided between adjacent rows of bond points 52. As such, both y and x can be varied to encourage tunnel formation and encourage meandering elastics 14. Alternatively as shown in FIG. 9, the protrusions can be staggered such that protrusions of a first series of adjacent rows are not staggered in the cross machine direction. This would encourage a straight run of elastics (at the to of FIG. 9), and downstream in the machine direction, a second series of adjacent rows can be staggered or offset by a distance x' to encourage a curved run (middle portion of FIG. 9), or the staggering of x' and y' can be more random resulting in a meandering pattern of elastics 14.

Figure 10:
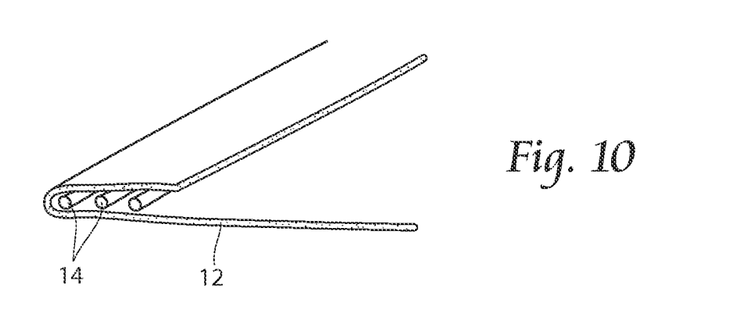
FIG. 10 is a perspective view of elastic material contained in a single material hem.

Referring now to FIG. 10 elastic material 14 can be used in the present invention by single material hem of material 12. In this manner, the meandered elastic will be captured between a laminate of the first material 12 portions after folding over an outboard portion of web 12, for instance by a folding plow (not shown).

Figure 11:
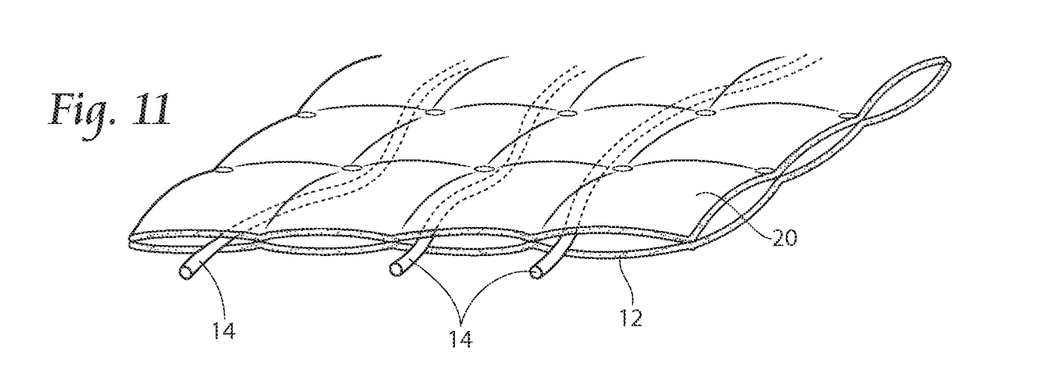
FIG. 11 is a perspective view of elastic material contained between two materials to create a trilaminate.

Referring now to FIG. 11, a perspective view of elastic material 14 contained between two materials 12 and 14 to create a trilaminate is shown. As can be seen, the elastic 14 meanders around bond points between material layers 12 and 14.

Figure 12:
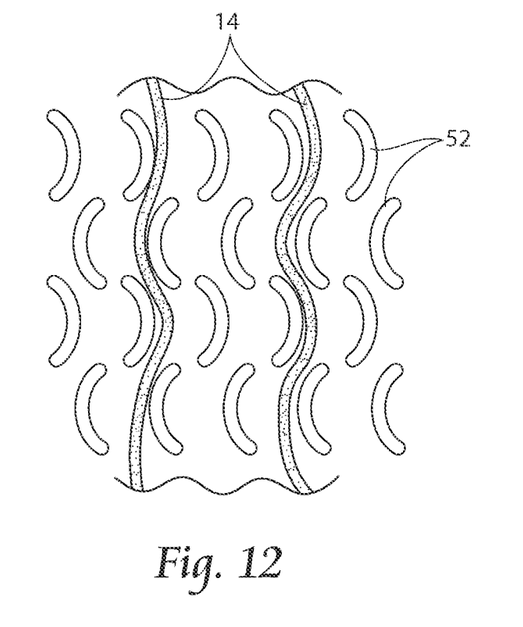
FIG. 12 is a fourth alternate anvil bond point configuration.

Referring now to FIG. 12 is a fourth alternate anvil bond point configuration is shown. A series of curved protrusions 56 can be used instead of or in addition to pins or protrusions 52 placed about an anvil roll 50 shown on FIGS. 4 and 5. In this embodiment, material layer 12 is introduced atop the roll 50, and carried in part by curved protrusions 56. Material layer 12 will somewhat drape over and about protrusions 56 to create channels encouraging elastic 14 to he laid down in a somewhat meandering pattern, such that when material layers 12 and 20 are bonded. (see, e.g., FIG. 4a), the bond points between material layers 12 and 20 will result in friction between elastic 14 meandering through the bond points of material layers 12 and 20. This friction prevents elastic 14 from sliding or creeping, i.e, elastic 14 is generally retained by frictional forces in its laid down meandering pattern.

Figure 13:
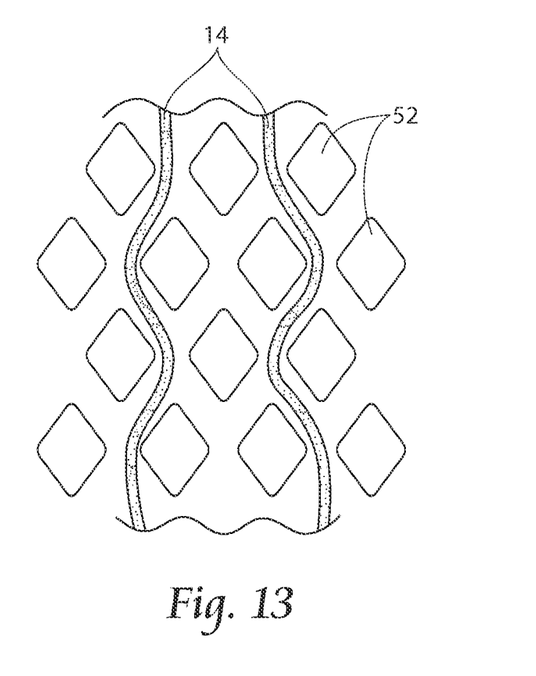
FIG. 13 is a fifth alternate anvil bond point configuration.

Referring now to FIG. 13, shaped protrusions 58, generally having preferably rounded corners to prevent material defects as a result of machine processing can be used. The shape of protrusions 58 can be changed, with the spacing between shapes, and the shapes of the protrusions 58 themselves changed to accommodate the creation of frictional holding forces between elastic 14 and material layers 12 and 20, specifically between elastic 11 and bonding points between material layers 12 and 20 which elastic 14 is sandwiched between. This configuration shows a larger surface area bond point, and a patterned profile of protrusions 52 is used to provide increased frictional resistance between elastic 14, the surrounding layers 12 and 20 and their bond points. In essence, a maze is provided for the elastic 14 to go through during manufacture, and rounded corners of protrusions 52 can urge the elastic 14 to be laid down in those maze patterns during the elastic laydown and bonding processes previously described.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A laminated material comprising:
  a first layer of material;
  a second layer of material;
  a first elastic strand disposed between said first and second layers of material;
  said first and second layers of material bonded together at spaced apart bond points;
  said first elastic strand disposed between said first and second layers of material in a non-linear manner, said first elastic strand meandering in a first direction around said spaced apart bond points and traversing a direction line extending in a second direction orthogonal to the first direction, said first elastic strand restrained from movement in at least one of said first direction and said second direction by friction with said first and second layers;
  said first elastic strand positioned between a pair of upstream bond points spaced apart in said first direction at a first upstream passage location, and positioned between a pair of downstream bond points spaced apart in said first direction at a first downstream passage location, said first upstream passage location offset from said first downstream passage location in said first direction;
  a second elastic strand disposed between said first and second layers of material;
  said second elastic strand positioned between a second pair of upstream bond points spaced apart in said first direction at a second upstream passage location, and positioned between a pair of downstream bond points spaced apart in said first direction at a second downstream passage location, said second upstream passage location offset from said second downstream passage location in said first direction;
  said elastic strands not intersecting said spaced apart bond points;
  wherein a width of said first and second elastic strands is less than a distance between said pair of upstream bond points and between said pair of downstream bond points and is less than a distance between said second pair of upstream bond points and between said second pair of downstream bond points, respectively, such that friction between said elastic strands and the first and second layers of material retain said elastic strands in place without a separate anchoring or affixing thereof to said first and second layers of material.

2. A laminated material according to claim 1, said first and second elastic strands restrained from movement in at least one of said first direction and said second direction by said bond points between said first and second layers.

3. A laminated material according to claim 1, said spaced apart bond points spaced apart at varying distances in said second direction.

4. A laminated material according to claim 1, said spaced apart bond points spaced apart at varying distances in said first direction.

5. A laminated material according to claim 1, said bond points comprising an irregular pattern of bond points.

6. A laminated material according to claim 1, said bond points configured to urge said elastic strands to lay in a meandering pattern between said bond points.

7. A laminated material according to claim 1, comprising a plurality of tunnels defined by said first and second layers of material and by said spaced apart bond points, with said first and second elastic strands are positioned within respective tunnels of said plurality of tunnels.

8. A laminated material according to claim 7, wherein positioning of said first and second elastic strands within respective tunnels of said plurality of tunnels and meandering of said first and second elastic strands in said first direction creates a frictional force between said first and second elastic strands and said first and second layers of material.

9. A laminated material according to claim 1, wherein said spaced apart bond points comprises columns of bond points extending generally in said second direction, with bond points in each column of bond points having an offset in said first direction.

10. A laminated material according to claim 1, wherein said spaced apart bond points comprises rows of bond points extending generally in said first direction, and wherein a spacing between bond points in a respective row varies from spacing between bond points in another respective row.

11. A laminated material according to claim 1, wherein said spaced apart bond points comprise curved bond points that create channels through which said first and second elastic strands meander.

12. The laminated material according to claim 1, wherein said spaced apart bond points define a plurality of tunnels positioned adjacent each other in said first direction.

13. A laminated material comprising:
a first layer of material and a second layer of material bonded together at a plurality of bond points that are spaced apart from one another, the first and second layers of material having a lengthwise direction and a crosswise direction; and
a first elastic strand disposed between the first and second layers of material, the first elastic strand oriented generally in the lengthwise direction and meandering in the crosswise direction around respective spaced apart bond points;
wherein the first elastic strand is positioned on a first crosswise side of a first bond point and is positioned on a second crosswise side opposite the first crosswise side of a second bond point that is spaced apart from the first bond point in the lengthwise direction; and
wherein the first elastic strand has a width less than a distance between adjacent bond points of the plurality of bond points as the first elastic strand passes between the adjacent bond points such that friction between the first elastic strand and the first and second layers of material retains the first elastic strand in place relative to the first and second layers of material.

14. The laminated material of claim 13 comprising a plurality of tunnels defined by the first and second layers of material and by the plurality of bond points, with the first elastic strand positioned within a respective tunnel of the plurality of tunnels.

15. The laminated material of claim 14 wherein positioning of the first elastic strand within a respective tunnel of the plurality of tunnels and meandering of the first elastic strand in the crosswise direction around respective spaced apart bond points creates a frictional force between the first elastic strand and the first and second layers of material.

16. The laminated material according to claim 15, wherein the frictional force between the first elastic strand and the first and second layers of material keeps the first elastic strand from creeping relative to the first and second layers.

17. The laminated material of claim 14 further comprising a second elastic strand disposed between the first and second layers of material.

18. The laminated material of claim 17 wherein the second elastic strand twisted together with the first elastic strand as entwined fibers positioned within a respective tunnel of the plurality of tunnels, so as to resist travel therethrough.

19. The laminated material of claim 17 wherein the second elastic strand is spaced apart from the first elastic strand in the crosswise direction, with the second elastic strand positioned on a first crosswise side of a third bond point and positioned on a second crosswise side opposite the first crosswise side of a fourth bond point that is spaced apart from the third bond point in the lengthwise direction.

* * * * *

UNITED STATES PATENT AND TRADEMARK OFFICE
CERTIFICATE OF CORRECTION

PATENT NO. : 10,792,194 B2  
APPLICATION NO. : 14/836698  
DATED : October 6, 2020  
INVENTOR(S) : Hohm et al.

Page 1 of 1

It is certified that error appears in the above-identified patent and that said Letters Patent is hereby corrected as shown below:

In the Specification

Column 2, Line 32, delete "leghole-elastic." and substitute therefore -- leg-hole elastic. --.

Column 7, Line 33, delete "(at the to of FIG. 9)," and substitute therefore -- (at the top of FIG. 9), --.

Column 8, Line 6, delete "elastic 11" and substitute therefore -- elastic 14 --.

Signed and Sealed this  
First Day of December, 2020

Andrei Iancu  
*Director of the United States Patent and Trademark Office*